United States Patent
Geiser et al.

(10) Patent No.: US 7,449,589 B2
(45) Date of Patent: Nov. 11, 2008

(54) PROCESS FOR PURIFYING (−)-Δ⁹-TRANS-TETRAHYDROCANNABINOL

(75) Inventors: Fiona Obrock Geiser, Glen Mills, PA (US); John James Keenan, Franklinville, NJ (US); Ronald Rossi, Mullica Hill, NJ (US); Albert Sanchez, Wilmington, DE (US); John Michael Whelan, Mount Lebanon, PA (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 10/584,122

(22) PCT Filed: Dec. 17, 2004

(86) PCT No.: PCT/GB2004/005394

§ 371 (c)(1), (2), (4) Date: Jul. 20, 2007

(87) PCT Pub. No.: WO2005/061480

PCT Pub. Date: Jul. 7, 2005

(65) Prior Publication Data

US 2007/0276031 A1  Nov. 29, 2007

(30) Foreign Application Priority Data

Dec. 23, 2003  (GB) ................. 0329635.7

(51) Int. Cl.
*C07D 311/80* (2006.01)
*A61K 31/352* (2006.01)

(52) U.S. Cl. ...................... 549/390; 514/455

(58) Field of Classification Search ................. 549/390; 514/455

See application file for complete search history.

(56) References Cited

U.S. PATENT DOCUMENTS 6,403,126 B1   6/2002  Webster et al.
2003/0050334 A1   3/2003  Murty et al.

FOREIGN PATENT DOCUMENTS

WO   WO-02/096899 A1   12/2002

OTHER PUBLICATIONS

Michael D. Cole, "Analysis of *Cannabis* by Supercritical Fluid Chromatograpy with Ultraviolet Detection," *Methods in Biotechnology*, vol. 13: *Supercritical Fluid Methods and Protocols*, Edited by J. R. Williams and A. A. Clifford (Humana Press, Inc., Totawa, NJ, 2000), pp. 145-148.

B. Bäckstrom et al., A preliminary study of the analysis of *Cannabis* by supercritical fluid chromatography with atmospheric pressure chemical ionisation mass spectroscopic detection, *Science & Justice*, 1997, vol. 37, No. 2, pp. 91-97.

T. Veress, "Sample preparation by supercritical fluid extraction for quantification—A model based on the diffusion-layer theory for determination of extraction time," *Journal of Chromatography A*, May 13, 1994, vol. 668, No. 2, pp. 285-291.

Shulamit Levin et al., "Resolution of chiral cannabinoids on amylose tris(3,5-dimethylphenylcarbamate) chiral stationary phase: effects of structural features and mobile additives," *Journal of Chromatography A.*, Nov. 12, 1993, vol. 654, No. 1, pp. 53-64.

Douglas W. Later et al., "Analysis of Various Classes of Drugs by Capillary Supercritical Fluid Chromatography," *Journal of Chromatographic Science*, vol. 24, Jun. 1986, pp. 249-253.

*Primary Examiner*—Bernard Dentz
(74) *Attorney, Agent, or Firm*—RatnerPrestia

(57) ABSTRACT

A process for separating (−)-Δ⁹-trans-tetrahydrocannabinol from a mixture of cannabinoids is disclosed. The process comprises at least one chromatographic step wherein a mobile phase passes trough a stationary phase. The stationary phase comprises a derivatised polysaccharide and the mobile phase comprises carbon dioxide.

13 Claims, 1 Drawing Sheet

(-)-Δ⁹-trans-THC (-)-Δ⁸-trans-THC (-)-Δ⁹-abn-THC (-)-Δ⁸-abn-THC

Cannabinol

"DPA-iso"

Cannabidiol

"DPA-triol"

PROCESS FOR PURIFYING (-)-Δ⁹-TRANS-TETRAHYDROCANNABINOL

This application is the U.S. National Phase application of PCT International Application No. PCT/GB2004/005394, filed Dec. 17, 2004, and claims priority of British Patent Application No. 0329635.7, filed Dec. 23, 2003.

FIELD OF THE INVENTION

The present invention relates to a process for purifying (-)-Δ⁹-trans-tetrahydrocannabinol. The compound is separated from a mixture of cannabinoids using a chromatographic technique.

BACKGROUND OF THE INVENTION (-)-Δ⁹-trans-tetrahydrocannabinol is the active ingredient in marijuana. It is used therapeutically as an inhalant or an oral drug for stimulation of appetite among AIDS and cancer chemotherapy patients. Tetrahydrocannabinols (THCs) can be isolated from marijuana (a mixture of leaves and flowering heads of the plant *Cannabis Sativa*). Alternatively, THCs can be obtained by synthetic routes, e.g. as described in WO 02/096899. Enantiomerically pure THCs are required for formulation into drug products, but the purification of THCs, whether produced by isolation or synthesis, is challenging. The present inventors have sought to provide a process for providing enantiomerically pure (-)-Δ⁹-trans-tetrahydrocannabinol ((-)-Δ⁹-THC).

Chromatographic techniques have been used to separate (-)-Δ⁹-THC from other cannabinoid compounds. The identification of cannabis products in drug samples has been achieved using Supercritical Fluid Chromatography. Such methods are described by Bäckström et al (Science & Justice, 1997, 37(2), 91-97), Cole ("Analysis of Cannabis by Supercritical Fluid Chromatography with Ultraviolet Detection", pages 145-148 in "Supercritical Fluid Methods and Protocols" ed. by Williams and Clifford), Veress (Journal of Chromatography A, 668 (1994), 285-291) and Later et al (Journal of Chromatographic Science, 1986, 24, 249-253). In these methods, very small samples (typically μg amounts) are analysed and the (-)-Δ⁹-THC is often destroyed during the detection step (e.g. by flame ionisation detection or by chemical ionisation mass spectrometry). These chromatographic methods achieve separation of (-)-Δ⁹-THC from other cannabinoid compounds, but are completely unsuitable for preparing sufficient quantities of enantiomerically pure (-)-Δ⁹-THC for incorporation into pharmaceutical products.

U.S. Pat. No. 6,403,126 addresses the problem of preparing (-)-Δ⁹-THC from marijuana. The patent describes the use of a supercritical fluid, such as carbon dioxide, as an extractant but not as an eluent in a chromatographic process. U.S. Pat. No. 6,403,126 does not demonstrate that (-)-Δ⁹-THC can be prepared using a supercritical fluid chromatographic process, and the only example uses a mobile phase of acetonitrile and water or methanol and water.

Levin et al (Journal of Chromatography A, 654 (1993), 53-64) have developed an analytical procedure for separating enantiomeric mixtures of cannabinoid compounds. The chromatographic method uses a Daicel Chiralpak® AD column, which is based on amylose tris(3,5-dimethylcarbamate) supported on macroporous silica gel. The mobile phase is n-hexane with ethanol or propanol. The enantioselective analysis determines the optical purity of samples but does not provide useful quantities of separated enantiomers.

SUMMARY OF THE INVENTION

Although chromatographic procedures have been used to analyse samples of cannabinoid compounds, an effective preparative separation of enantiomerically pure (-)-Δ⁹-THC has not been demonstrated. The present inventors have devised a chromatographic process that can be used to prepare quantities of enantiomerically pure (-)-Δ⁹-THC for incorporation into pharmaceutical products.

DETAILED DESCRIPTION OF THE INVENTION

Figure 1:
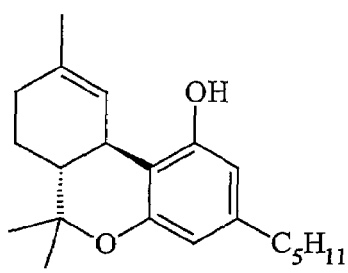
FIG. 1 shows the chemical structures of (-)-Δ⁹-trans-tetrahydrocannabinol and a number of impurities that may be found in it.
Figure 1:
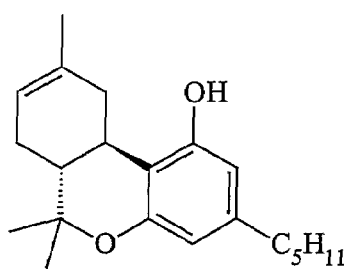
Figure 1:
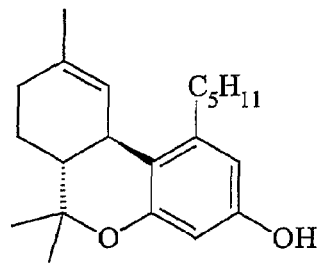
Figure 1:
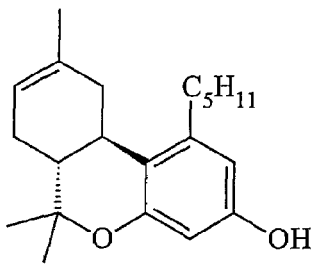
Figure 1:
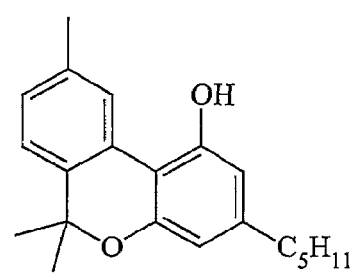
Figure 1:
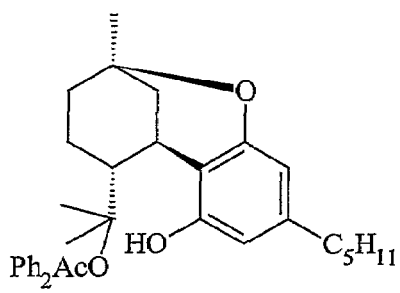
Figure 1:
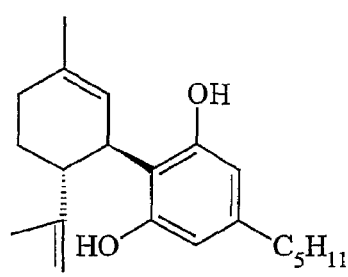
Figure 1:
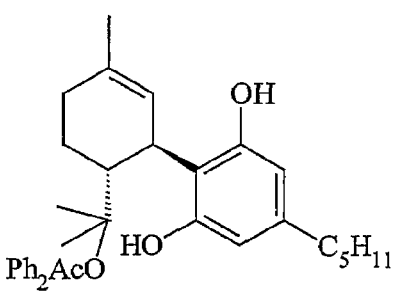

Accordingly, the present invention provides a preparative separation process wherein (-)-Δ⁹-trans-tetrahydrocannabinol is separated from a mixture of cannabinoids, wherein the process comprises at least one chromatographic step wherein a mobile phase passes through a stationary phase, characterised in that the stationary phase comprises a derivatised polysaccharide and the mobile phase comprises carbon dioxide.

The inventors have found that a chromatographic process combining a derivatised polysaccharide stationary phase and a carbon dioxide-containing mobile phase provides an effective preparative separation of (-)-Δ⁹-THC. By "preparative separation process" we mean a process that is capable of providing at least 0.1 g of purified product, preferably at least 1 g of purified product in a reasonable timeframe, i.e. less than a day.

Preferably the mobile phase in the present invention is a mixture of carbon dioxide and one or more modifiers. The modifier can be any liquid solvent such as an alcohol, ethyl acetate, acetonitrile or methylene chloride. The modifier should be compatible with the stationary phase, e.g. ethyl acetate and methylene chloride cannot be used with a Chiralpak AD column as they will destroy the column. The modifier is suitably a $C_1$-$C_5$ alcohol, most preferably ethanol. A carbon dioxide and ethanol mobile phase has been found to be particularly advantageous. When (-)-Δ⁹-THC is prepared according to the synthetic route outlined in WO 02/096899, one of the impurities is "DPA-iso" (see FIG. 1 for the chemical structure). When the mobile phase is carbon dioxide/ethanol, the DPA-iso elutes before the (-)-Δ⁹-THC. A minor impurity eluting in front of a major component usually focuses due to the effects of displacement chromatography, so it was possible to remove all of the DPA-iso. Using an alternative heptane/ethanol mobile phase, the DPA-iso eluted after the (-)-Δ⁹-THC. It is considerably more difficult to resolve minor components eluting in the tail of a major component, so the carbon dioxide/ethanol mobile phase provides a significantly improved process compared to heptane/ethanol.

Carbon dioxide is easily removed, so the (-)-Δ⁹-THC product can be provided as a solution with the modifier as a solvent. It may therefore be desirable to choose a modifier in which the (-)-Δ⁹-THC is stable.

The ratio of carbon dioxide to modifier, as a weight (g) to volume ($cm^3$) is suitably in the range 100:1 to 50:50, preferably in the range 95:5 to 75:25, most preferably in the range 85:15 and 75:25. The ratio of carbon dioxide to modifier can be varied during the chromatographic process.

The stationary phase comprises a derivatised polysaccharide and is a solid chiral stationary phase. The derivatised polysaccharide is suitably immobilised on a substrate such as silica gel, zirconium, alumina, ceramics or other silicas, and is preferably immobilised on silica gel. Examples of derivatised polysaccharides include amylosic, cellulosic, chitosan, xylan, curdlan, dextran and inulan classes of polysaccharides. The amylosic polysaccharides are preferred. A particularly preferred stationary phase is amylose tris(3,5-dimethylphenylcarbamate) supported on macroporous silica gel, which is available as Chiralpak® AD, manufactured by Daicel Chemical Co. Another preferred stationary phase is Chiralpak® IA, which is similar to Chiralpak ® AD but has an immobilised chiral selector so that a wider variety of solvents can be used.

The stationary phase is preferably an encapsulated derivatised polysaccharide; the polysaccharide groups are not bonded to a substrate. It is thought that the encapsulated stationary phase may prevent decomposition of the (−)-$\Delta^9$-THC to (−)-$\Delta^8$-THC.

In a preferred embodiment of the invention the process comprises a further chromatographic step wherein a mobile phase passes through a stationary phase, wherein the stationary phase is an achiral stationary phase and is suitably selected from silica gel and derivatised silica gels, wherein the silica is derivatised with aminopropylsiloxane, diol-substituted propylsiloxane or 2-ethylpyridine siloxane groups. The 2-ethylpyridine siloxane immobilised on a silica support (shown below) is a preferred achiral stationary phase because the (−)-$\Delta^9$-THC does not degrade to form (−)-$\Delta^8$-THC, as was observed with some achiral stationary phases.

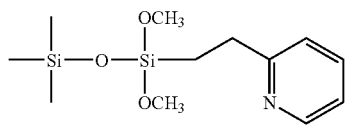

The further chromatographic step ensures removal of the impurity (−)-$\Delta^9$-abn-THC (see FIG. 1 for the chemical structure) from a mixture of cannabinoids.

In the further chromatographic step, the mobile phase suitably comprises a mixture of carbon dioxide and one or more modifiers. The modifier can be any liquid solvent but is suitably a $C_1$-$C_5$ alcohol, most preferably ethanol. The ratio of carbon dioxide to modifier, as a weight (g) to volume ($cm^3$) is suitably in the range 100:1 to 50:50, preferably in the range 100:1 to 75:25, most preferably in the range 95:5 and 90:10. The ratio of carbon dioxide to modifier can be varied during the chromatographic process.

Suitably a first chromatographic step uses the achiral stationary phase, preferably 2-ethylpyridine siloxane immobilised on a silica support and a second chromatographic step uses the derivatised polysaccharide stationary phase, and most preferably amylose tris(3,5-dimethylphenylcarbamate) supported on macroporous silica gel. It is preferred to use an amylosic stationary phase after a 2-ethylpyridine siloxane phase because it has been found that the amylosic phase can be destroyed by solvent impurities that might be present in the crude cannabinoid feed, whereas the 2-ethylpyridine siloxane is more robust. However, pure (−)-$\Delta^9$-THC can also be achieved by reversing the two steps, i.e. using the 2-ethylpyridine siloxane phase after the amylosic phase.

Suitable chromatographic apparatus is well known to the skilled person. It is preferred to use apparatus that is suitable for Supercritical Fluid chromatography such as the Novasep Supersep 10 SFC or the Novasep Supersep 100 SFC. The crude feed containing the mixture of cannabinoids is periodically injected into the apparatus wherein the mobile phase flows through the stationary phase which is located in a column. After detection at the column outlet, the purified fractions of the feed are directed to different traps. The carbon dioxide is removed from the purified fractions and is preferably recycled. Detection at the column outlet can be conducted by measuring UV absorption at an appropriate wavelength.

The column diameter is suitably from 0.5 cm to 50 cm and the column length is suitably from 5 cm to 50 cm. The particle size of the stationary phase is typically from 5 to 50 μm.

The process is suitably carried out at temperatures from 5 to 45° C. and at elevated pressures, e.g. from 80 bar to 300 bar. Typical flow rates depend upon the diameter of the column, and may vary from, e.g. 10 g to 4 kg/min.

In a further aspect the present invention provides a process for preparing a pharmaceutical product comprising (−)-$\Delta^9$-THC, wherein the process comprises a first step wherein (−)-$\Delta^9$-THC is separated from a mixture of cannabinoids by a preparative separation process according to the invention, and a further step wherein the (−)-$\Delta^9$-THC is combined with pharmaceutical carriers to form the pharmaceutical product. Suitable pharmaceutical carriers are known to the skilled person.

The following examples are illustrative but not limiting of the invention.

Crude Feed (−)-$\Delta^9$-trans-tetrahydrocannabinol was prepared as described in WO 2//096899.The crude reaction product included a variety of cannabinoid impurities, which are shown with (−)-$\Delta^9$-trans-THC in FIG. 1. The crude reaction product was dissolved in ethanol to provide the crude feed.

EXAMPLE 1

Two Step Purification using a 2-ethylpyridine Siloxane Column and a Chiralpak AD Column Chromatographic Apparatus A Novasep Supersep 10 SFC was used in both chromatographic steps. Two stationary phases were used: a 2-ethylpyridine siloxane stationary phase, manufactured by Princeton Chromatography Inc, with a particle diameter of 10 μm, and a Chiralpak AD stationary phase (amylose tris(3,5-dimethylphenylcarbamate) supported on macroporous silica gel), manufactured by Daicel Chemical Co., with a particle diameter of 20 μm. The chromatographic steps were carried out at 25° C. and at a pressure of 100bar.

Step 1:

Chromatographic Separation using a 2-ethylpyridine Siloxane Column

The crude feed was filtered through 0.2 micrometer filter (Whatman PTFE w/GMF) and injected onto a chromatography column (length 25cm, inner diameter 2.1cm) containing 2-ethylpyridine siloxane stationary phase at a column flow rate of 40 g/min using a mobile phase of 92% carbon dioxide and 8% ethanol. Column injections on the column were 0.85 ml of crude feed injected for 5 seconds. After 128 column injections over 48 hours, an ethanolic solution was recovered with a (−)-$\Delta^9$-trans-THC concentration of about 25 g/l. After removal of ethanol by rotary evaporation at 30° C. under vacuum, about 22.5g of semi-purified (−)-$\Delta^9$-trans-THC was recovered exhibiting greater than 95% purity.

Step 2:

Chromatographic Separation using a Chiralpak AD Column

The semi-purified (−)-$\Delta^9$-trans-THC was re-dissolved in absolute ethanol to a concentration of about 300 g/l to produce a feed for injection onto Chiralpak AD column (length 25cm, inner diameter 2.1cm) at a column flow rate of 40g/min using a mobile phase of 80% carbon dioxide and 20% ethanol. After 60 column injections of 0.85ml (over 5 seconds) of the semi-purified feed, an ethanolic solution was recovered (about 2.2 liters) and stored in a freezer for solvent evaporation at a later date. The estimated recovery of purified (−)-$\Delta^9$-trans-THC (>99.5% purity) was ~15 grams.

EXAMPLE 2

Two Step Purification using a Chiralpak AD Column and a 2-ethylpyridine Siloxane Column Chromatographic Apparatus The apparatus was the same as the apparatus used in Example 1.

Step 1:

Chromatographic Separation using a Chiralpak AD Column

The crude feed was filtered through 0.2 micrometer filter (Whatman PTFE w/GMF) and injected onto a chromatography column (length 25 cm, inner diameter 2.1cm) containing Chiralpak AD stationary phase at a column flow rate of 40g/min using a mobile phase of 80% carbon dioxide and 20% ethanol. After 35 column injections of 0.85ml, 6g of semi-purified (−)-$\Delta^9$-trans-THC (97.4% purity) were collected. The majority of the remaining impurity was found to be (−)-$\Delta^9$-abn-THC (2.5% AUC).

Step 2:

Chromatographic Separation using a 2-ethylpyridine Siloxane Column

The semi-purified (−)-$\Delta^9$-trans-THC was injected onto Chiralpak AD column (length 25cm, inner diameter 1cm) at a column flow rate of 20g/min using a mobile phase of 92% carbon dioxide and 8% ethanol. After 3 second column injections at 5ml/min of the semi-purified feed, (−)-$\Delta^9$-abn-THC impurity was reduced to less than 0.05% AUC.

Comparative Example 1

One Step Purification using a Chiralpak AD Column and a Hexane/Ethanol Mobile Phase The chromatographic apparatus was the same as the apparatus used in Example 1. The crude feed was filtered through 0.2 micrometer filter (Whatman PTFE w/GMF) and injected onto a chromatography column (length 25cm, inner diameter 1cm) containing Chiralpak AD stationary phase at a column flow rate of 4.8ml/min using a mobile phase of 95% hexane and 5% ethanol. Preparative purification of (−)-$\Delta^9$-trans-THC from the DPA-iso impurity was not achieved.

EXAMPLE 3

Scaled-up Two Step Purification using a 2-ethylpyridine Siloxane Column and a Chiralpak AD Column Chromatographic Apparatus A Novasep Supersep 100 SFC was used in both chromatographic steps. Two stationary phases were used: a 2-ethylpyridine siloxane stationary phase, manufactured by Princeton Chromatography Inc, with a particle diameter of 10 μm, and a Chiralpak AD stationary phase (amylose tris(3,5-dimethylphenylcarbamate) supported on macroporous silica gel), manufactured by Daicel Chemical Co., with a particle diameter of 20μm.

Step 1:

Chromatographic Separation using a 2-ethylpyridine Siloxane Column

The Novasep Supersep 100 SFC was fitted with a 100mm inner diameter dynamic axial compression (DAC) column packed to a bed length of 250mm length with 2-ethylpyridine bonded silica. A mixture of liquid carbon dioxide (Airgas, Instrument Grade) and Absolute Ethanol (Warner Graham, USP Grade) in a ratio of about 96:4 wt/wt were used as the mobile phase. The operating conditions were:

| | | |
|---|---|---|
| Column Temperature: | 30° | C. |
| Column Pressure: | 125 | Bar |
| Liquid $CO_2$ flow rate: | 1770 | g/min |
| Ethanol flow rate: | 80 | g/min |
| Detection: | UV 245 | nm |

The product was concentrated in ethanol eluent by evaporation resulting in an amber solution. (−)-$\Delta^9$-trans-THC was isolated with a purity >96%.

Step 2:

Chromatographic Separation using a Chiralpak AD Column

The Novasep Supersep 100 SFC was fitted with a 100mm inner diameter dynamic axial compression (DAC) column packed to a bed length of 250mm length with Chiralpak AD. A mixture of liquid Carbon Dioxide (Airgas, Instrument Grade) and Absolute Ethanol (Warner Graham, USP Grade) in a ratio of about 86:14 wt/wt were used as the mobile phase. The SFC operating conditions were:

| | | |
|---|---|---|
| Column Temperature: | 25° | C. |
| Column Pressure: | 125 | Bar |
| Liquid CO2 flow rate: | 858 | g/min |
| Ethanol flow rate: | 142 | g/min |
| Detection: | UV 245 | nm |

The product was concentrated in ethanol eluent by evaporation resulting in a colourless solution. (−)-$\Delta^9$-trans-THC was isolated with a purity >99%.

The invention claimed is:

1. A process for separating $(-)-\Delta^9$-trans-tetrahydrocannabinol from a mixture comprising it and other cannabinoids, wherein the process is a preparative separation process that comprises performing on the mixture at least one chromatographic step comprising passing a mobile phase comprising carbon dioxide through a stationary phase comprising a derivatised polysaccharide, and wherein the process is capable of providing at least 0.1 gram of the separated $(-)-\Delta^9$-trans-tetrahydrocannabinol in less than a day.

2. A process according to claim 1, wherein the mobile phase is a mixture of carbon dioxide and one or more modifiers.

3. A process according to claim 2, wherein the mobile phase is a mixture of carbon dioxide and ethanol.

4. A process according to claim 3, wherein the ratio of carbon dioxide to liquid modifier is in the range 95:5 to 75:25.

5. A process according to claim 1, wherein the derivatised polysaccharide is immobilised on a substrate selected from the group consisting of silica gel, zirconium, alumina, ceramics and other silicas.

6. A process according to claim 1, wherein the stationary phase comprises an amylosic polysaccharide.

7. A process according to claim 6, wherein the stationary phase is amylose tris(3,5-dimethylphenylcarbamate) supported on macroporous silica gel.

8. A process according to claim 1, wherein the process comprises a further chromatographic step comprising passing a mobile phase through an achiral stationary phase.

9. A process according to claim 8, wherein the achiral stationary phase is 2-ethylpyridine siloxane immobilised on a silica support.

10. A process according to claim 8, wherein the chromatographic step using the achiral stationary phase is performed before the chromatographic step using the stationary phase comprising a derivatised polysaccharide.

11. A process according to claim 8, wherein the chromatographic step using the stationary phase comprising a derivatised polysaccharide is performed before the chromatographic step using the achiral stationary phase.

12. A process for preparing a pharmaceutical product, comprising a first step of separating $(-)-\Delta^9$-trans-tetrahydrocannabinol from a mixture comprising it and other cannabinoids by a process according to claim 1, and a further step comprising combining the separated $(-)-\Delta^9$-trans-tetrahydrocannabinol with one or more pharmaceutical carriers to form the pharmaceutical product.

13. The process of claim 1, wherein the process is capable of providing at least 1 gram of the separated $(-)-\Delta^9$-trans-tetrahydrocannabinol in less than a day.

* * * * *